United States Patent [19]

Suzuki

[11] 4,228,305

[45] Oct. 14, 1980

[54] PROCESS FOR PREPARING ACETIC ACID DERIVATIVES

[75] Inventor: Shigeto Suzuki, San Francisco, Calif.

[73] Assignee: Chevron Research Company, San Francisco, Calif.

[21] Appl. No.: 36,473

[22] Filed: May 7, 1979

Related U.S. Application Data

[63] Continuation-in-part of Ser. No. 861,070, Dec. 15, 1977, abandoned.

[51] Int. Cl.² .............................................. C07C 59/06
[52] U.S. Cl. ..................................... 562/579; 562/518
[58] Field of Search ................................ 562/518, 579

[56] References Cited

U.S. PATENT DOCUMENTS

| | | | |
|---|---|---|---|
| 2,211,693 | 8/1940 | Flaherty | 560/179 |
| 3,911,003 | 10/1975 | Suzuki | 562/518 |
| 3,948,977 | 4/1976 | Suzuki | 562/579 |

OTHER PUBLICATIONS

Kirk–Othmer, "Encyclopedia of Chemical Technology", 1 Ed. vol. 6, pp. 877–878, (1950), Interscience, Publ.

*Primary Examiner*—Natalie Trousof
*Assistant Examiner*—L. Hendriksen
*Attorney, Agent, or Firm*—D. A. Newell; John Stoner, Jr.; A. T. Bertolli

[57] ABSTRACT

A process for preparing glycolic acid which comprises contacting formaldehyde with formic acid in the presence of hydrogen fluoride present in an amount to serve as both catalyst and solvent for the reactants and reaction mixture.

4 Claims, No Drawings

PROCESS FOR PREPARING ACETIC ACID DERIVATIVES

CROSS-REFERENCE TO RELATED APPLICATION

This application is a continuation-in-part of application Ser. No. 861,070, filed Dec. 15, 1977, now abandoned.

BACKGROUND OF THE INVENTION

This invention concerns a process for preparing glycolic acid. In particular, the process concerns the preparation of glycolic acid (hydroxyacetic acid) by the reaction of formaldehyde and formic acid catalyzed with liquid hydrogen fluoride.

The reaction of formaldehyde, carbon monoxide and water to produce hydroxyacetic acid is well known. For instance, U.S. Pat. Nos. 2,152,852; 2,153,064; and 2,265,945 disclose the use of acid catalysts, such as hydrochloric, sulfuric, and phosphoric acids, to promote the reactions under elevated temperature and pressure. Because the reaction requires relatively harsh conditions, attempts to improve the process have generally focused upon optimized concentrations of reactants and conditions or more effective catalysts. U.S. Pat. No. 3,911,003 granted Oct. 7, 1975 describes the preparation of hydroxyacetic acid by the hydrogen fluoride catalyzed reaction of formaldehyde and carbon monoxide in an aqueous environment. According to these patents the use of catalytic amounts of hydrogen fluoride provides very high yields of acid product under relatively mild reaction conditions.

Thus, the efficiency of the process for preparing acetic acid derivatives such as hydroxyacetic acid from formaldehyde, carbon monoxide, and water has been found to be surprisingly dependent upon the choice of catalyst.

It is also well known that formic acid, when heated in the process of concentrated sulfuric acid, decomposes into carbon monoxide and water. The mechanism of decomposition is described by Noller (Ed.) in the *Chemistry of Organic Compounds*, 3rd (1966) at pages 174 and 187:

"Because the carboxyl group is united to a hydrogen atom, rather than to a carbon atom as in all subsequent members of the series, formic acid undergoes a number of special reactions. When mixed with concentrated sulfuric acid, it decomposes into carbon monoxide and water."

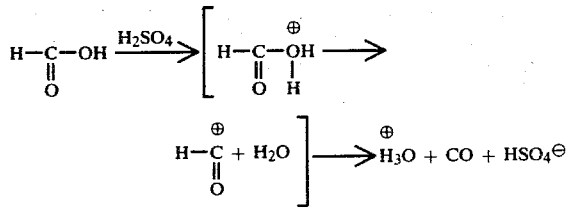

Thus, the decomposition of formic acid is caused by hydrogen ion attack on the negative oxygen of the formic acid molecule. Sulfuric acid, having a pK of 1.92 in aqueous solution readily provides hydrogen ion. Accordingly, the decomposition of formic acid is a special reaction catalyzed by a particular acid having a relatively high dissociation constant. For this reason formic acid is not generally accepted as a substitute for carbon monoxide and water in reactions catalyzed by relatively weak acids.

Nonetheless, formic acid is readily available and it would be an advantage to substitute formic acid for carbon monoxide and water in the process for preparing glycolic acid from formaldehyde, carbon monoxide, and water.

SUMMARY OF THE INVENTION

It has now been found that glycolic acid can be prepared in high yields under mild conditions by contacting formaldehyde and formic acid in the presence of a catalytic and solvent amount of hydrogen fluoride. The process is carried out at a temperature of from about 0° C. to about 100° C. at ambient pressure.

DETAILED DESCRIPTION OF THE INVENTION

Among other factors the present invention is based upon the surprising discovery that under mild conditions formaldehyde and formic acid will react in the presence of a catalytic amount of hydrogen fluoride to form high yields of glycolic acid. This reaction can be represented by the formula

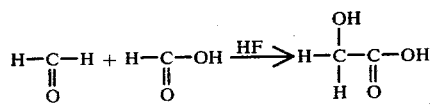

The reaction is carried out under mild conditions in the liquid phase. Suitable temperatures may vary from about 0° C. to about 100° C., preferably from about 10° C. to about 60° C. At lower temperatures, below the boiling point of the mixture, atmospheric pressure (i.e., zero psig) is sufficient although reduced or increased pressure can be used, depending on temperature. In general, a pressure of from about 10 psig to about 100 psig is suitable. When the temperature is above the boiling point of the mixture a closed vessel is used, and the autogeneous pressure developed is sufficient to effect reaction. Under these mild conditions the reaction is surprisingly rapid, often running to completion in as little as about 2 hours.

The process is catalyzed by liquid hydrogen fluoride. In addition, the hydrogen fluoride also serves as a medium or solvent for the reactants. Suitable amounts of hydrogen fluoride for carrying out the reaction range from about 40 to 93%, preferably 50 to 70%, by weight, based on total weight of reaction mixture, namely formic acid, formaldehyde, HF and water. The hydrogen fluoride may contain other constituents such as up to 10% by weight, biased on hydrogen fluoride, of metal salts, e.g., copper oxides, silver oxide, and nickel oxide or up to 20%, by weight, based on hydrogen fluoride of other halogen acids such as hydrobromic and hydrochloric acids, or of boron hydrogen tetrafluoride, HBF. HBF. is a particularly preferred additional constituent which may be added as boron trifluoride. The presence of HBF. increases the reaction rate but complicates product separation. The formic acid reactant can be added to an excess of hydrogen fluoride and the liquids passed either cocurrently or countercurrently to a formaldehyde gas stream. In this way, the process can be carried out at a continuous or batch operation.

Formaldehyde may be used in its various forms but in this process is preferably trioxane. Aqueous formaldehyde solutions, for example, commercially available formalin containing 40% formaldehyde are equally as useful. The molar ratio of formaldehyde, on a water-free basis, to formic acid is not critical and generally ranges from about 1:2 to about 2:1, a ratio of about 1:1 is preferred.

Product recovery and purification are accomplished by conventional methods. For instance, the entire bottoms product after water removal can be esterified and the esters separated by distillation. Hydrolysis of the ester will give an aqueous solution of glycolic acid. A preferred method is to distill the crude reaction mixture to remove overhead the hydrogen fluoride, water and any unreacted formaldehyde and/or formic acid, leaving a crude glycolic acid bottoms fraction. The bottoms contain a substantial amount of glycolyl glycolates and other glycolic acid values, which can be hydrolyzed to obtain glycolic acid as a conventional water solution.

Glycolic acid is difunctional in that it contains both a carboxyl group and a hydroxyl group. Many uses for this product are based upon this dual functionality. For example, the hydroxyl group may be oxidized to a carbonyl group to produce glyoxalic acid or to a carboxyl group to produce oxalic acid; the carboxyl group may be esterified and reduced to produce ethylene glycol. The hydroxyl group is readily replaced by halogen upon reaction with hydrogen halide. Glycolic acid is used as a monomer in the preparation of polyglycolic acid, a preferred material for suture fibers.

The following examples further illustrate the invention and suggest alternate embodiments with the scope of the claims which follow.

EXAMPLES

Example 1

Preparation of Hydroxy-Acetic Acid

A 300 ml Monel metal stirred autoclave was charged with 40 grams (2.0 mols) of liquid hydrogen fluoride, 9.2 grams (0.2 mols) of formic acid and 4.5 grams (0.15 mol of formaldehyde) of trioxane. This mixture was heated under autogenous pressure for 2 hours at 53° C.

At the end of this time, the hydrogen fluoride was removed by inert gas stripping under reduced pressure. The remaining crude product was esterified with methanol and was found to contain 52% glycolic acid as determined by gas liquid chromatography analysis.

EXAMPLES 2–12

Other preparations were carried out in essentially the manner as in Example 1. The experimental conditions and results are given in Table I.

TABLE I

The HF Catalyzed Reaction of Formic Acid With Formaldehyde

| | Reactants (Mols) | | | Conditions | | Product | | |
|---|---|---|---|---|---|---|---|---|
| | | | | | | Conversion, %[1] | | Yield, %[1] |
| Ex. No. | Formaldehyde | Acid | HF | Temp. °C. | Time, Hrs. | Formaldehyde | Acid | Glycolic Acid |
| 2 | 0.15 | Formic Acid, 0.15 | 2.0 | 50 | 1 | 80 | 77 | 87, 90 |
| 3 | 0.15 | Formic Acid, 0.15 | 2.0 | 50 | 2 | 93 | 89 | 77, 81 |
| 4 | 0.15 | Formic Acid, 0.30 | 2.0 | 50 | 2 | 94 | 50 | 87, — |
| 5 | 0.30 | Formic Acid, 0.10 | 2.5 | 50 | 2 | — | 99 | —, 77 |

[1] First value based on formaldehyde, the second on acid.

What is claimed is:

1. A process for preparing glycolic acid which comprises contacting a reaction mixture comprising formaldehyde, formic acid and liquid hydrogen fluoride catalyst at a temperature of from about 0° C. to about 100° C.

2. A process according to claim 1 carried out at a pressure of about 0 to 100 psig.

3. A process according to claim 2 wherein the molar ratio of formaldehyde to formic acid is from about 1:2 to about 2:1 and the amount of hydrogen fluoride is from about 40 to 93%, by weight, based on the reaction mixture.

4. A process according to claim 3 wherein the molar ratio of formaldehyde to formic acid is about 1:1 and the amount of hydrogen fluoride is from about 50 to 70%, by weight, based on the reaction mixture.

* * * * *

UNITED STATES PATENT AND TRADEMARK OFFICE
CERTIFICATE OF CORRECTION

PATENT NO. : 4,228,305
DATED : October 14, 1980
INVENTOR(S) : Shigeto Suzuki

It is certified that error appears in the above-identified patent and that said Letters Patent are hereby corrected as shown below:

Column 1, line 40, "process" should read --presence--.

Column 2, line 56, "biased" should read --based--.

Column 2, lines 60-61, "HBF.   HBF." should read --$HBF_4$.   $HBF_4$--.

Column 2, line 63, "HBF." should read --$HBF_4$--.

Column 4, line 6 of Table I, "Nc." should read --No.--.

Signed and Sealed this

First Day of September 1981

[SEAL]

Attest:

GERALD J. MOSSINGHOFF

Attesting Officer    Commissioner of Patents and Trademarks